United States Patent [19]

Bendiner

[11] Patent Number: 5,412,090

[45] Date of Patent: May 2, 1995

[54] HYDROUS CELLULOSE PULP FOR NON PAPER PRODUCTS

[76] Inventor: Bernard Bendiner, 8815 W. Golf Rd., Suite 12D, Niles, Ill. 60714

[21] Appl. No.: 190,301

[22] Filed: Feb. 2, 1994

[51] Int. Cl.[6] .......................... A61K 7/06; A61K 7/16; A61K 7/50

[52] U.S. Cl. ........................................ 536/56; 162/5; 424/49; 424/70.13; 252/14; 252/32; 252/89.1; 252/108; 252/128; 252/130; 252/DIG. 13; 252/DIG. 5; 252/DIG. 10

[58] Field of Search .............. 162/5; 536/56; 514/781, 514/846, 881; 424/49, 70; 252/128, 130, DIG. 5, DIG. 10, DIG. 13, 14, 32, 89.1, 108

[56] References Cited

U.S. PATENT DOCUMENTS

| | | | |
|---|---|---|---|
| 2,703,754 | 3/1955 | Myers | 162/5 |
| 3,248,277 | 4/1966 | Gärtner | 162/5 |
| 3,808,089 | 4/1974 | Von Koeppen et al. | 162/5 |
| 3,822,178 | 7/1974 | Von Koeppen et al. | 162/5 |
| 4,202,878 | 5/1980 | Ritze | 424/49 |
| 4,570,573 | 2/1986 | Lohman | 119/1 |
| 4,654,207 | 3/1987 | Preston | 424/70 |

FOREIGN PATENT DOCUMENTS

| | | |
|---|---|---|
| 131681 | 5/1946 | Australia . |
| 0174825 | 3/1986 | European Pat. Off. . |
| 940250 | 10/1963 | United Kingdom . |

*Primary Examiner*—Ronald W. Griffin
*Attorney, Agent, or Firm*—Willian Brinks Hofer Gilson & Lione

[57] ABSTRACT

A method for improving products such as toothpaste, shampoo, soap, detergent and lotions or creams and such improved products. The products are improved by adding a hydrous cellulose pulp that has an unlimited shelf life to the product. The hydrous cellulose pulp is resistant to decomposition and can be produced either by recycling waxed paper or through a process that begins with virgin vegetable constituents and wax. During the defibering process an emulsifier is added to the slurry and its temperature is elevated to 150°–190° Fahrenheit.

14 Claims, No Drawings

HYDROUS CELLULOSE PULP FOR NON PAPER PRODUCTS

BACKGROUND OF THE INVENTION

This invention relates to a process for producing pulp, having unique proprieties, from virgin wood constituents or from waxed paper and using the pulp as an additive for non-paper industry type products such as toothpaste, shampoo, soap, detergent and lotions or creams. The pulp also can be used for toys, ground cover and to simulate snow.

Most paper is made from plant fiber, most often wood, in a process that separates the cellulose from the other plant fiber material. Cellulose, the major constituent of plant fibers, is a carbohydrate. Carbohydrates are convertible into glucose by hydrolysis; a chemical process of decomposition. Under appropriate conditions the bacteria present in the paper making process contributes to and hastens decomposition. As a result, cellulose pulp material maintained in a hydrous state has a very short shelf life.

In the paper making process, water is driven from the cellulose pulp and the remaining fiber is dried in one continuous operation. Thus decomposition of the cellulose pulp is not a problem. However, if the process is suspended with the cellulose pulp in the hydrous state, for example over 90% water, the pulp has a very short shelf life. This short shelf life has been a major obstacle to the development of non-paper industry uses for hydrous cellulose pulp. Generally speaking, hydrous cellulose pulp is vulnerable to decomposition regardless whether the pulp is derived from virgin vegetable constituents or from a paper recycling operation.

Waxed paper is customarily manufacture by forming the paper sheet first then treating the sheet with an application of wax coating, either in dry or liquid form. For example, molten paraffin wax is easily applied by continuously passing a paper sheet through a molten bath of wax, removing the excess and then chilling. Such waxed papers have excellent resistance to water vapor, are free from odor, taste and toxicity and are low in cost.

At one time waste waxed paper presented problems in the paper recycling industry. When waste wax paper was recycled waxy spots would appear on the resulting recycled paper and a wax coating would collect on the equipment thus fouling the recycling process. Consequently, the resulting recycled paper was considered inferior and it was often necessary to stop the process so that the equipment could be adequately cleaned.

The problem, with recycling waste waxed paper, was solved however by adding a water dispersible non-ionic emulsifiers to the pulper during the repulping phase of the recycling process. The mixture containing the emulsifier is mechanically agitated at a temperature sufficiently high to melt the wax, for example from approximately 150° to 190° Fahrenheit. This process produced an emulsified wax-fiber slurry having a solids consistency of from approximately 4% to 6% by weight. U.S. Pat. Nos. 3,808,089 and 3,822,178, the disclosures of which are incorporated herein by reference, fully discloses the above described process. As is discussed in U.S. Pat. No. 3,822,178, the water soluble non-ionic emulsifiers used in the process are selected from the group consisting of polyethylene glycol ethers of hydrophobic alcohols, alkylphenoxy polyethoxyethanols, fatty acid amides and mixtures thereof and meet the following emulsion stability standard. Emulsifiers for practicing this invention include: the ethoxylated aliphatic alcohols wherein the alcohol is a hydrophobic secondary alcohol having from 11 to 15 carbon atoms and wherein the average molar ratio of ethylene oxide to hydrophobic alcohol is in a range of 5:1 to 15:1; ethoxylated alkyl phenols in which the ratio of moles of ethylene oxide per mole or ethylene oxide per mole of alkyl phenol is in the range of 7–8 inclusive; ethoxylated alkyl phenols in which the alkyl substituent is linear; and the fatty acid amide diethanol amine condensates derived from a member selected from the group consisting of myristic acid, lauric acid, palmitic acid, stearic acid and mixtures thereof.

The hydrous cellulose pulp produced in this process for recycling waste waxed paper has the property of an unlimited shelf life.

SUMMARY OF THE INVENTION

It is an object of this invention to utilize hydrous cellulose pulp that has an unlimited shelf life in processes and products outside of the paper industry.

It is another object of this invention to provide a method for improving toothpaste, shampoo, soap, detergent lotions and cream products by adding hydrous cellulose pulp that has an unlimited shelf life when the product is in liquid form such that the pulp can become dispersed evenly throughout the product.

It is a further object of this invention to provide a process for improving toothpaste, shampoo, soap, detergent lotions and cream products that include the steps of repulping waxed paper in a process requiring an emulsifier and heat sufficient to melt the wax to thus provide a micro-molecular film on the fiber and then dispersing the fiber in the product when it is in a liquid form.

It is a still further object of this invention to provide a hydrous cellulose pulp material that, at temperatures above freezing, simulates snow.

It is a further object of this invention to provide a mulch for plants that will maintain a high moisture level and can be dyed such that its color can be earthen or be coordinated with the plant's color.

It is a further object of this invention to improve the efficiency of toothpaste in both its ability to cleanse teeth and its ability to stimulate and condition the gums by a process that include the steps of forming hydrous cellulose pulp that has an unlimited shelf life in the presence of wax in a process requiring an emulsifier and heat: for increasing the temperature sufficient to melt the wax to thus provide a micro-molecular film on the fiber and then blend and disperse the fiber in the toothpaste.

It is a further object of this invention to provide a process for improving products such as mouthwash or glass cleaners that have a low viscosity that include the steps of forming hydrous cellulose pulp that has an unlimited shelf life from material in the presence of wax in a process requiring an emulsifier and heat for increasing the temperature sufficient to melt the wax to thus provide a micro-molecular film on the fiber and then blend and disperse the fiber such that it becomes suspended in the product.

It is a further object of this invention to provide a process for improving lotions and creams that include the steps of forming hydrous cellulose pulp that has an unlimited shelf life from material in the presence of wax in a process requiring an emulsifier and heat for increasing the temperature sufficient to melt the wax to thus provide a micro-molecular film on the fiber and then blend and disperse the fiber in the lotion or cream.

DETAILED DESCRIPTION OF THE PREFERRED EMBODIMENT

During the emulsification phase, of the wax paper recycling process used in practicing this invention, substantial quantities of wax are present from the waste waxed paper. However, this wax does not contaminate or coat the equipment even when slurries containing the emulsified product are cooled. When making waxed paper, very little wax penetrates below the surface of the unwaxed sheet of paper. However, during the emulsification phase of recycling, the paper is broken down into minute fiber filaments having irregularly shaped surfaces. Each of these minute filaments has a substantial surface area. Literally millions of fiber filaments are released from a relatively small piece of wax paper. Consequently, a piece of waxed paper having a waxed surface of 100 square inches, for example, releases fiber filaments into the emulsified slurry that have a surface area that may be as much as 1,000,000 times the original 100 square inches, or 10,000,000 square inches. The wax from the surface of the waxed paper, is melted during the emulsification phase and forms a very thin micro-molecular film on the fiber filaments. As a result of this micro-molecular film, paper products made in accordance with this product are characterized by the complete absence of glossy specks even though they were formed from 100% high wax content stock. Thus, although the original wax is still present after the emulsification process, its presence is not apparent. In the past, the pulp formed in this process was used exclusively in the paper industry for making high quality recycled paper products. However a dramatic change has occurred in the cellulose pulp, it is no longer vulnerable to decomposition. The very thin micro-molecular film on the fibers produced in this process has rendered the cellulose pulp immune from the hydrolysis process that normally converts it to glucose and to attack by bacteria. The hydrous cellulose pulp now has an unlimited shelf life at normal temperatures and conditions.

This bacteria resistent hydrous cellulose pulp, which possesses an unlimited shelf life, may be produced either by recycling waste waxed paper, new waxed paper or by processing virgin vegetable constituents in the presence of wax during the emulsification phase of the defibering process.

As a result of this invention, non-paper industry uses have been developed for hydrous cellulose pulp possessing fibers coated with a thin micro-molecular layer of wax.

The fiber material derived from this process can be combined with products such as toothpaste, shampoo, soap, detergent and lotions or creams in liquid form such that the fiber particles become suspended evenly throughout the detergent and soap and greatly enhance the cleaning property of the detergent and soap.

The fiber material derived from this process can be used to produce a moisture retaining plant mulch that can be color coordinated with the plant.

The fiber material derived from this process can be used to simulate snow, from which realistic snow balls can be made in temperatures above freezing or the simulated snow can be used for skiing in warm climates.

The micro-molecular film on the cellulose fiber filaments prevents decomposition and result in an unlimited shelf life. Furthermore, the filaments will not contaminate other materials to which they are added.

In accordance with this invention, an example of the starting waxed paper that can be used is the type used in bakeries and deli-contestants to wrap food products. Waxed paper of this type is coated with a food grade paraffin wax, designated as a dry wax. Waste waxed paper can be used in the preferred embodiment and is obtained directly from the paper producing facilities. For example, trimmings from a trimming machine or wax paper that did not meet required test standards may be used. Such waxed paper is free of printing and thus is clean. The waxed paper is added to a pulper. A pulper is basically a vat for receiving a material that can be agitated by mechanical means and includes means to control the temperature. The process of pulping is essentially one of separating cells from intercellular material. It should be understood that any equipment such as a conventional high speed pulper may be used. The temperature of the wax-containing fiber slurry is raised to a temperature above the melting point of the wax and beating is continued until the wax and fiber are released into the aqueous solution. The resulting water-fiber slurry can then be subjected to a washing process to remove any impurities. Newly manufactured waked paper does not need this washing process.

The process of the present invention encompasses the use of 100% waxed paper stock having a wax content of up to 30% by weight. However, non-waxed waste paper, in modest proportions can be used without affecting the outcome. Non waxed fiber products can be used as a starting product and a paraffin wax in the correct ratio to fiber added. The use of waxed paper as a starting point has the advantage that it contains the proper ratio of fiber to wax and it is available at economical rates.

The water soluble non-ionic emulsifier that is added to the slurry being from the group consisting of: polyethylene glycol ethers of hydrophobic alcohols; alkylphenoxy polyethoxyethanols; fatty acid amides and mixtures thereof. The water soluble non-ionic emulsifier must also meet specific emulsion stability standards and depending upon the ultimate product it may be necessary that it comply with Food and Drug Administration requirements. The preferred water soluble non-ionic emulsifiers include: ethoxylated aliphatic alcohols wherein the alcohol is a hydrophobic secondary alcohol having from 11 to 15 carbon atoms and wherein the average molar ratio of ethylene oxide to hydrophobic alcohol is in a range of 5:1 to 15:1; ethoxylated alkyl phenols in which the ratio of moles of ethylene oxide per mole or ethylene oxide per mole of alkyl phenol is in the range of 7–8 inclusive; ethoxylated alkyl phenols in which the alkyl substituent is linear; and the fatty acid amide diethanol amine condensates derived from a member selected from the group consisting of myristic acid, lauric acid, palmitic acid, stearic acid and mixtures thereof.

After the hydrous cellulose pulp has been coated with the micro-molecular film, it can be mixed with products such as toothpaste, shampoo, soap, detergent and lotions or creams. Thus wax from the original waste waxed paper is present on the fiber filaments that are dispersed in the final product. However, such wax is present on the fibers filaments, in a finely divided form. The finely divided, dispersed wax on the fiber filaments in the detergent and soap product does not interfere with dispersion of the fiber in the liquid detergent and soap. In products such as liquid soap and shampoo the fiber filaments become suspended in the liquid and do not settle out. In products that are more viscus, such as a mouthwash or a glass cleaner the product must be treated, for example by running the product through a colloid mill, to maintain its suspension. When the fiber containing detergent and soap solution is used as a shampoo, for example, the dispersed fibers function as scouring elements that rub and massage the hair filaments to thereby greatly enhancing the cleaning properties of the detergent and soap solution.

In addition to shampoo this invention has been used as an additive to toothpaste, mouthwash, shaving cream, car washing detergents, dish-washing compounds, laundry detergents, industrial hand detergent and soap and liquid facial soap or lotion. In all of these applications the wax coated fiber filaments functions to improve the effectiveness of the basic cleaning agent.

The resulting hydrous cellulose pulp material is stable and will not melt at temperatures above 32° Fahrenheit, is white in color and has a moisture content of about 90%. Simulated snow balls can be made from the hydrous cellulose pulp material by grasping a hand full of the material, packing it between the palms of the hands such that a small portion of the water is squeezed out and the resulting product can be thrown in the same fashion as a snow ball, There are children in parts of this country and in the world who have never had the opportunity to make and throw snow balls. A product for making simulated snow balls will be a fascinating toy for children in such regions. Also simulated snow can be used for skiing during the summer or for use at ski resorts when the temperature is above freezing.

A characteristics of the resulting hydrous cellulose pulp is its ability of retaining a high percent of water. A plant mulch has been developed from the resulting hydrous cellulose pulp that not only prevents the growth of weeds but is very beneficial in providing moisture for the plant over extended periods. Moisture from the mulch is absorbed by the soil at a rate that the moisture can be utilized by the plant. Since the hydrous cellulose pulp does not decompose, when the hydrous cellulose pulp becomes water depleted, it can be resaturated and the process repeated. Another advantage of this product is that the resulting hydrous cellulose pulp readily accepts dyes and thus can be dyed any of a desired colors, The resulting hydrous cellulose pulp has been dyed, Kelly green, and found to be a very attractive mulch for house plants. The Kelly green color being considered more attractive then the usual black or brown color of the soil. It is also contemplated that mulch could be produced in colors that are coordinated with the color of the flowers.

The following are examples of products which have been improved through the use of this invention. Shampoo made in accordance with this invention has resulted in an improved product that leaves the hair feeling softer and having a brighter appearance. In addition the amount of hair that is collected in a hair brush that is used after grooming with the improved product is reduced. Furthermore shampoo made in accordance with this invention functions to detangle the hair and has been found to be particular beneficial when used on difficult to manage hair such as hair that is course and kinky.

Shampoo that especially formulated for animals such as dogs and horses that has been improved in accordance with this invention has been found to be greatly improved especially because of its improved ability to detangle and soften the appearance of the hair.

Skin creams have been improved in accordance with this invention and conditions such as "ash" have been greatly improved or eliminated.

When toothpaste that has been improved in accordance with this invention is used, a marked reduction in bleeding of the gums and plaque build up has been noted.

When shaving creams are improved in accordance with this invention, closer shaves and a smoother shaven surface are obtained.

While the invention has heretofore been described in detail with particular reference to specific products, it is to be understood that variation, modifications and the use of equivalents can be effected without departing from the scope of this invention. It is, therefore, intended that such changes and modifications be covered by the following claims.

I claim:

1. A process for improving mouthwash, glass cleaner, toothpaste, shampoo, soap, detergent and lotions or creams comprising the steps of:
    (a) producing a decomposition resistant hydrous cellulose pulp, the individual fibers of which are coated with a thin wax film;
    (b) adding the decomposition resistent hydrous cellulose pulp to the product while the product is in liquid form;
    (c) blending the resulting mixture such that the fibers of the decomposition resistance hydrous cellulose pulp are dispersed and suspended in the product where they function as scrubbing and massaging agents to enhance the cleaning and conditioning function of the product.

2. The invention as set forth in claim 1 wherein in the process for producing the decomposition resistant hydrous cellulose pulp a water soluble non-ionic emulsifier that meets the following emulsion stability standards is used:
    ethoxylated aliphatic alcohols wherein the alcohol is a hydrophobic secondary alcohol having from 11 to 15 carbon atoms and wherein the average molar ratio of ethylene oxide to hydrophobic alcohol is in a range of 5:1 to 15:1.

3. The invention as set forth in claim 1 wherein in the process for producing the decomposition resistant hydrous cellulose pulp a water soluble non-ionic emulsifier that meets the following emulsion stability standards is used:
    ethoxylated alkyl phenols in which the ratio of moles of ethylene oxide per mole or ethylene oxide per mole of alkyl phenol is in the range of 7-8 inclusive.

4. The invention as set forth in claim 1 wherein in the process for producing the decomposition resistant hydrous cellulose pulp a water soluble non-ionic emulsifier that meets the following emulsion stability standards is used:
    ethoxylated alkyl phenols in which the alkyl substituent is linear.

5. The invention as set forth in claim 1 wherein in the process for producing the decomposition resistant hydrous cellulose pulp a water soluble non-ionic emulsifier that meets the following emulsion stability standards is used:

the fatty acid amide diethanol amine condensates derived from a member selected from the group consisting of myristic acid, lauric acid, palmitic acid, stearic acid and mixtures thereof.

6. Mouthwash, glass cleaner, toothpaste, shampoo, soap, detergent, lotions or creams having an additive dispersed and suspended therein, each fiber of the additive acting as a scrubbing and massaging agent as the product is applied to the surface to be cleaned or conditioned;

said additive being a decomposition resistant wax coated hydrous cellulose pulp.

7. The invention as set forth in claim 6 wherein said decomposition resistant hydrous cellulose pulp is made in a process in which a water soluble non-ionic emulsifier that meets the following emulsion stability standards was used:

ethoxylated aliphatic alcohols wherein the alcohol is a hydrophobic secondary alcohol having from 11 to 15 carbon atoms and wherein the average molar ratio of ethylene oxide to hydrophobic alcohol is in a range of 5:1 to 15:1.

8. The invention as set forth in claim 6 wherein said decomposition resistant hydrous cellulose pulp is made in a process in which a water soluble non-ionic emulsifier that meets the following emulsion stability standards was used:

ethoxylated alkyl phenols in which the ratio of moles of ethylene oxide per mole or ethylene oxide per mole of alkyl phenol is in the range of 7–8 inclusive.

9. The invention as set forth in claim 6 wherein said decomposition resistant hydrous cellulose pulp is made in a process in which a water soluble non-ionic emulsifier that meets the following emulsion stability standards was used:

ethoxylated alkyl phenols in which the alkyl substituent is linear.

10. The invention as set forth in claim 6 wherein said decomposition resistant hydrous cellulose pulp is made in a process in which a water soluble non-ionic emulsifier that meets the following emulsion stability standards was used:

the fatty acid amide diethanol amine condensates derived from a member selected from the group consisting of myristic acid, lauric acid, palmitic acid, stearic acid and mixtures thereof.

11. A method of producing simulated snow from hydrous cellulose pulp material that has high water retention, that is stable and has an unlimited shelf life comprising the steps of:

a) providing a hydrous cellulose pulp material comprising fibers and having a water content of about 90%; and (b) covering each fiber of said hydrous pulp material with a thin wax coating to prevent decomposition thereof.

12. The method as set forth in claim 11 wherein said simulated snow has the additional property that a portion of its water content can be squeezed out to simulate snow being packed.

13. A method of producing a mulch for plants from hydrous cellulose pulp material that has high water retention, that is stable and has an unlimited shelf life comprising the steps of:

(a) providing a hydrous cellulose pulp material comprising fibers and having a water content of about 90%; and (b) covering each fiber of said hydrous cellulose pulp material with a thin wax coating to prevent decomposition thereof.

14. The method as set forth in claim 13 wherein said mulch for plants is dyed to an earthen color or a color that coordinates with plants for which it is functioning as a mulch.

* * * * *